(12) United States Patent
Hernandez et al.

(10) Patent No.: US 12,161,339 B2
(45) Date of Patent: *Dec. 10, 2024

(54) APPLICATORS FOR MODULAR MAGNETIC ANASTOMOSIS DEVICE

(71) Applicant: IRCAD, Strasbourg (FR)

(72) Inventors: Juan Hernandez, Strasbourg (FR); Michele Diana, Lingolsheim (FR)

(73) Assignee: IRCAD, Strasbourg (FR)

( * ) Notice: Subject to any disclaimer, the term of this patent is extended or adjusted under 35 U.S.C. 154(b) by 212 days.

This patent is subject to a terminal disclaimer.

(21) Appl. No.: 16/861,050

(22) Filed: Apr. 28, 2020

(65) Prior Publication Data

US 2021/0007744 A1 Jan. 14, 2021

Related U.S. Application Data

(63) Continuation of application No. 14/654,643, filed as application No. PCT/IB2013/003246 on Dec. 20, 2013, now Pat. No. 10,682,143.

(60) Provisional application No. 61/794,782, filed on Mar. 15, 2013, provisional application No. 61/740,865, filed on Dec. 21, 2012.

(51) Int. Cl.
| | | |
|---|---|---|
| *A61B 17/11* | (2006.01) | |
| *A61B 17/34* | (2006.01) | |
| *A61B 17/00* | (2006.01) | |
| *A61B 17/30* | (2006.01) | |

(52) U.S. Cl.
CPC ...... *A61B 17/1114* (2013.01); *A61B 17/3421* (2013.01); *A61B 17/3468* (2013.01); *A61B 2017/00876* (2013.01); *A61B 2017/1117* (2013.01); *A61B 2017/1139* (2013.01); *A61B 2017/306* (2013.01); *A61B 2017/3484* (2013.01); *A61B 2017/3488* (2013.01)

(58) Field of Classification Search
CPC .......... A61B 17/1152; A61B 2017/348; A61B 2017/3482; A61B 2017/306; A61B 2017/3488; A61M 25/0009
See application file for complete search history.

(56) References Cited

U.S. PATENT DOCUMENTS

| | | |
|---|---|---|
| 4,197,840 A | 4/1980 | Beck et al. |
| 5,667,488 A | 9/1997 | Lundquist et al. |

(Continued)

FOREIGN PATENT DOCUMENTS

| | | |
|---|---|---|
| CN | 1582857 A | 2/2005 |
| EP | 2086426 A2 | 8/2009 |

(Continued)

OTHER PUBLICATIONS

EP Patent Application No. 12811240.6 Extended European Search Report mailed Jun. 9, 2015.

(Continued)

*Primary Examiner* — Anh T Dang

(74) *Attorney, Agent, or Firm* — Wilson Sonsini Goodrich & Rosati

(57) ABSTRACT

The present disclosure provides description of applicators to implement modular magnetic anastomosis device. In one embodiment the delivery device is a laparoscopic instrument for MISS surgery, in another embodiment the delivery device is endoscopy or colonoscopy instrument for NOTES surgery.

12 Claims, 20 Drawing Sheets

(56) References Cited

U.S. PATENT DOCUMENTS

| | | | |
|---|---|---|---|
| 5,817,062 A | 10/1998 | Flom et al. | |
| 5,891,159 A | 4/1999 | Sherman et al. | |
| 6,110,187 A * | 8/2000 | Donlon | A61B 17/12036 606/151 |
| 6,352,543 B1 | 3/2002 | Cole | |
| 8,092,378 B2 | 1/2012 | Roth et al. | |
| 10,568,630 B2 | 3/2020 | Hernandez et al. | |
| 11,344,308 B2 | 5/2022 | Hernandez et al. | |
| 2002/0147385 A1 | 10/2002 | Butler et al. | |
| 2003/0222117 A1 * | 12/2003 | Orban, III | A61B 17/115 227/176.1 |
| 2005/0283235 A1 | 12/2005 | Kugler et al. | |
| 2006/0235368 A1 | 10/2006 | Oz | |
| 2006/0263145 A1 | 11/2006 | Pal | |
| 2007/0135803 A1 | 6/2007 | Belson | |
| 2007/0167868 A1 | 7/2007 | Sauer | |
| 2007/0255165 A1 | 11/2007 | Uesugi et al. | |
| 2007/0276378 A1 | 11/2007 | Harrison et al. | |
| 2007/0299310 A1 * | 12/2007 | Phillips | A61B 1/04 600/127 |
| 2008/0161644 A1 | 7/2008 | Ghabrial | |
| 2008/0200933 A1 | 8/2008 | Bakos et al. | |
| 2009/0078736 A1 * | 3/2009 | Van Lue | A61B 17/115 227/175.1 |
| 2009/0125042 A1 * | 5/2009 | Mouw | A61B 17/1114 606/153 |
| 2010/0076573 A1 | 3/2010 | Kugler et al. | |
| 2010/0161040 A1 | 6/2010 | Braido et al. | |
| 2010/0331625 A1 * | 12/2010 | Rosemurgy | A61B 1/00154 600/116 |
| 2011/0160752 A1 | 6/2011 | Aguirre | |
| 2011/0295055 A1 * | 12/2011 | Albrecht | A61B 17/00234 604/9 |
| 2011/0295285 A1 * | 12/2011 | Mcweeney | A61B 17/1114 606/153 |
| 2012/0197062 A1 | 8/2012 | Requarth | |
| 2013/0253550 A1 * | 9/2013 | Beisel | A61B 17/1114 606/153 |
| 2015/0342608 A1 | 12/2015 | Hernandez | |
| 2016/0022266 A1 | 1/2016 | Lukin et al. | |
| 2016/0262761 A1 | 9/2016 | Beisel et al. | |
| 2019/0274687 A1 | 9/2019 | Wang et al. | |

FOREIGN PATENT DOCUMENTS

| | | | |
|---|---|---|---|
| EP | 2934347 | A2 | 10/2015 |
| JP | 2006271832 | A | 10/2006 |
| JP | 4681920 | B2 | 5/2011 |
| SU | 736966 | A1 | 5/1980 |
| WO | WO-9802099 | A1 | 1/1998 |
| WO | WO-2004096013 | A2 | 11/2004 |
| WO | WO-2008061024 | A2 | 5/2008 |
| WO | WO-2008101075 | A2 | 8/2008 |
| WO | WO-2008101075 | A3 | 3/2009 |
| WO | WO-2009048954 | A1 | 4/2009 |
| WO | WO-2014102621 | A2 | 7/2014 |

OTHER PUBLICATIONS

European Patent Application No. 13861506.7 Communication dated Aug. 30, 2017.
European Patent Application No. 19174351.7 Extended European Search Report dated Jul. 18, 2019.
International Search Report and Written Opinion for PCT Patent Application No. PCT/US2012/046272 issued Oct. 1, 2012.
Jamshidi et al.: Magnamosis: Magnetic compression anastomosis with comparison to suture and staple techniques. J.Pediatr. Surg., 44(1):222-228 (2009).
PCT Patent Application No. PCT/IB2013/003246 International Preliminary Report on Patentability mailed Jul. 2, 2015.
PCT/IB2013/003246 International Search Report and Written Opinion dated Feb. 5, 2015.
U.S. Appl. No. 14/237,521 Final Office Action dated Mar. 7, 2019.
U.S. Appl. No. 14/237,521 Office Action dated Dec. 1, 2016.
U.S. Appl. No. 14/237,521 Office Action dated Jun. 14, 2016.
U.S. Appl. No. 14/237,521 Office Action dated Jun. 16, 2017.
U.S. Appl. No. 14/237,521 Office Action dated May 10, 2018.
U.S. Appl. No. 14/237,521 Office Action mailed Sep. 29, 2015.
U.S. Appl. No. 14/654,643 Office Action dated Jan. 17, 2017.
U.S. Appl. No. 14/654,643 Office Action dated Oct. 31, 2018.
U.S. Appl. No. 14/654,643 Office Action dated Sep. 27, 2017.
U.S. Appl. No. 14/654,653 Final Office Action dated Jul. 9, 2019.
European Patent Application No. 13861506.7 Office Action dated Jun. 10, 2021.
U.S. Appl. No. 17/727,595 Non-Final Office Action dated Oct. 5, 2022.
U.S. Appl. No. 16/717,915 Office Action dated Jul. 7, 2021.
U.S. Appl. No. 16/717,915 Restriction Requirement dated Apr. 29, 2021.

* cited by examiner

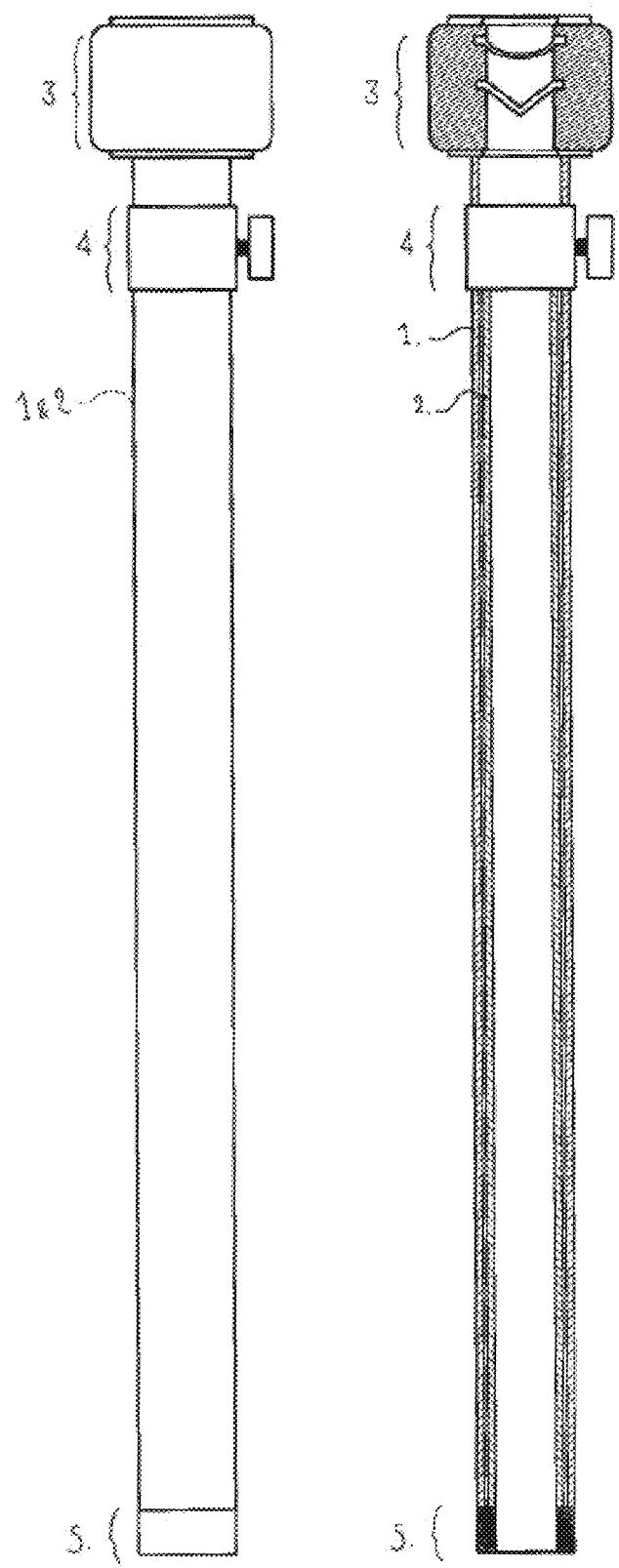

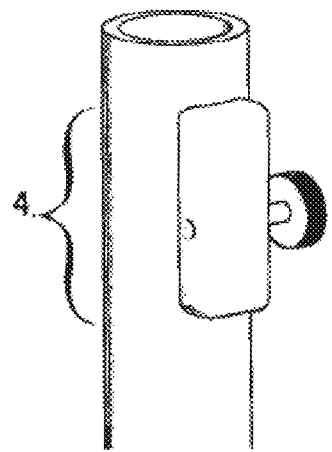 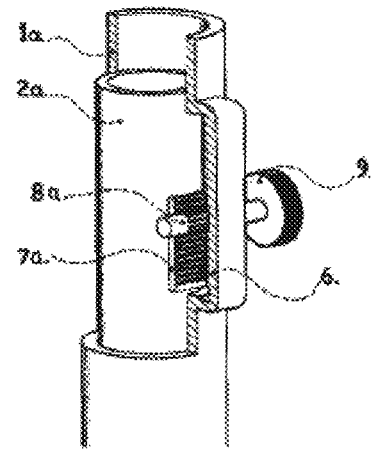 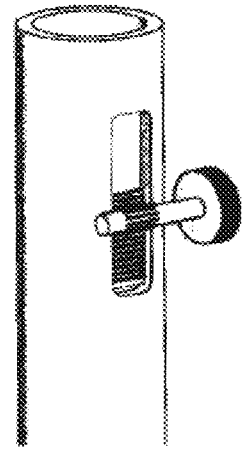
Figure 15  Figure 16  Figure 17
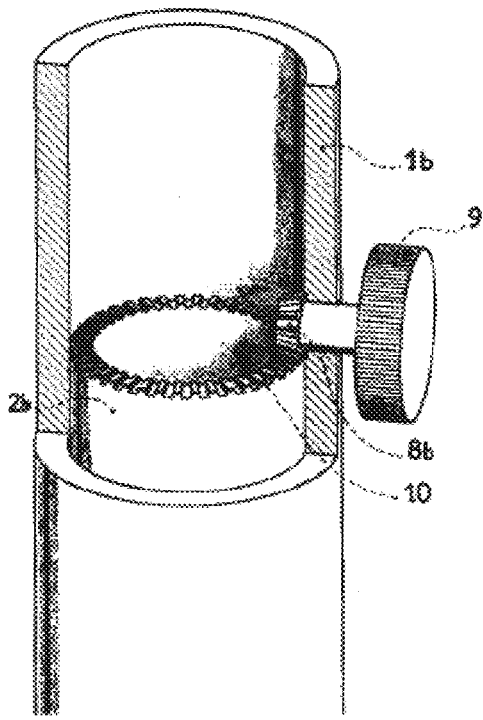
Figure 18

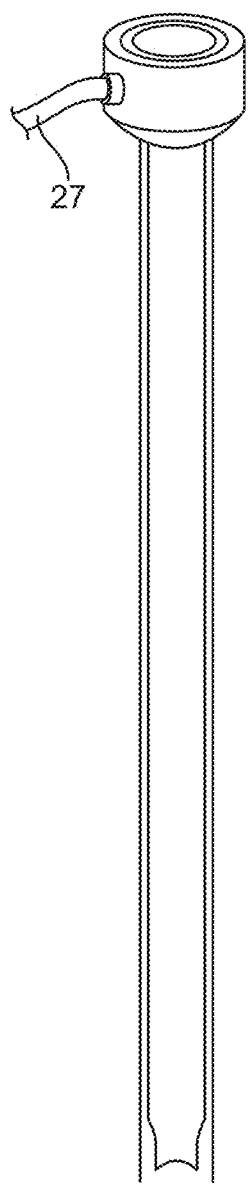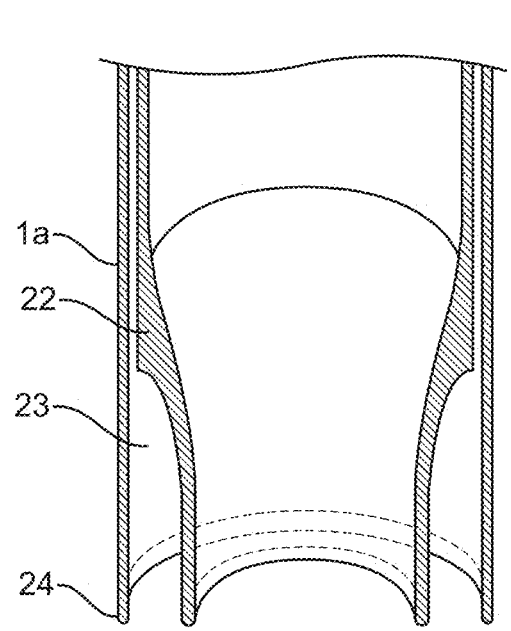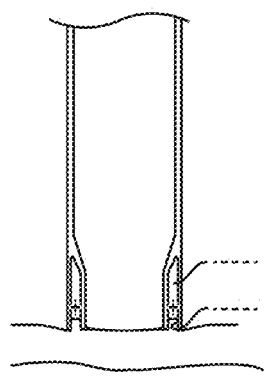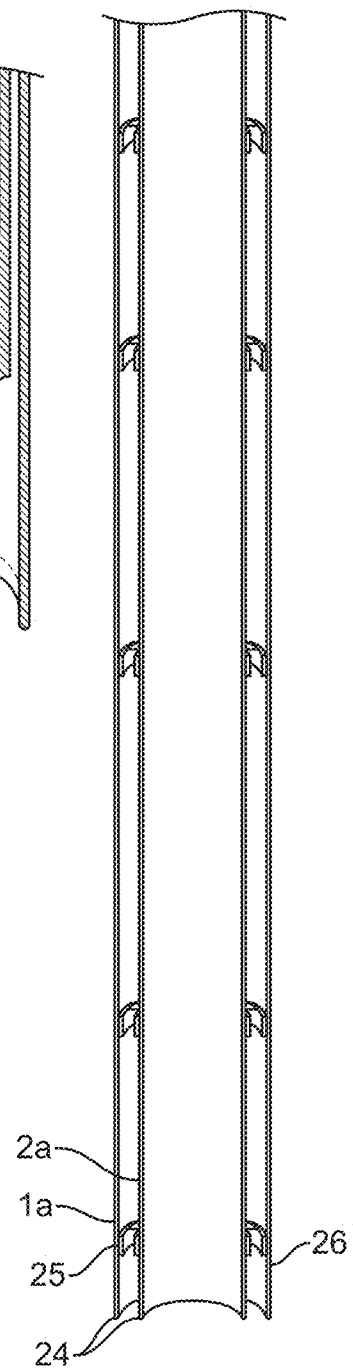
FIG. 26
FIG. 27
FIG. 28
FIG. 29

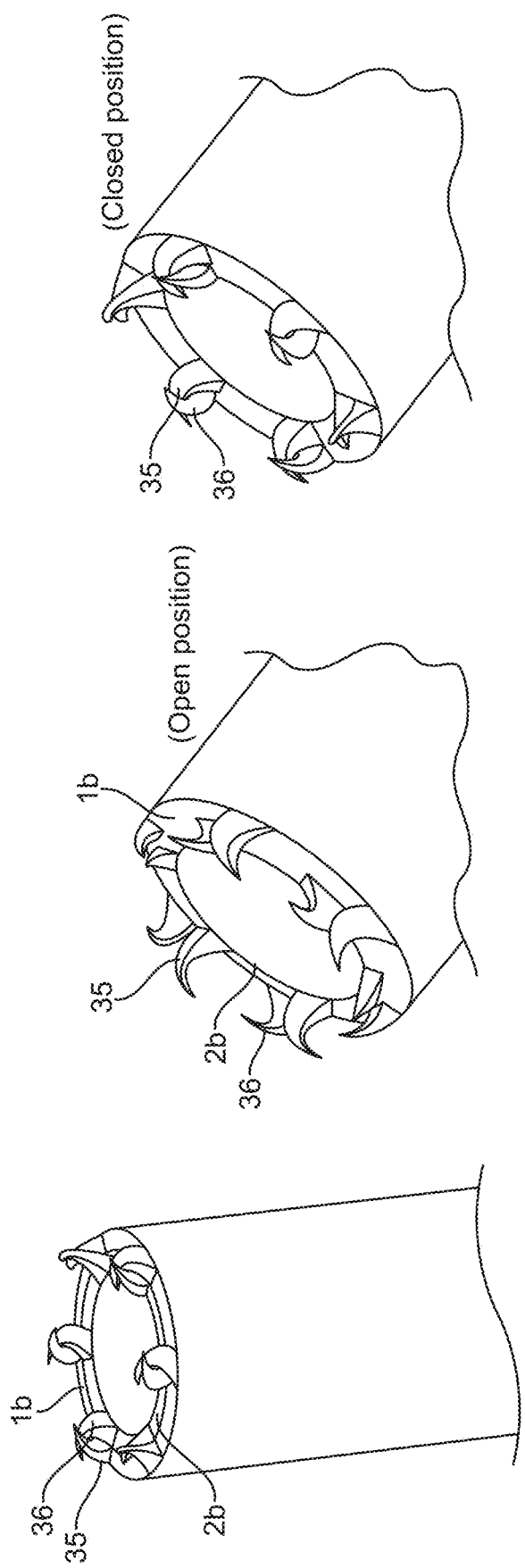

APPLICATORS FOR MODULAR MAGNETIC ANASTOMOSIS DEVICE

CROSS-REFERENCE

This application is a continuation of U.S. application Ser. No. 14/654,643, filed Jun. 22, 2015, which is a National Stage Entry of International Patent Application PCT/IB2013/003246, filed Dec. 20, 2013, which claims the benefit of U.S. Provisional Patent Application No. 61/740,865, filed Dec. 21, 2012, and U.S. Provisional Patent Application No. 61/794,782, filed Mar. 15, 2013, each of which is incorporated herein by reference in its entirety.

BACKGROUND OF THE INVENTION

The present invention relates to an applicator and methods particularly useful for the delivery of injection medical devices by minimally invasive single site surgery (MISS), natural orifice transluminal endoscopic surgery or colonoscopic surgery (NOTES™).

In one embodiment, the injection device is a modular magnetic anastomosis device.

In one embodiment, the applicator is a laparoscopic instrument.

In an additional embodiment the laparoscopic instrument has is comprised of:
a) an exterior tube, b) an interior tube, c) a sealing system, d) an actuation system, e) a stowing system.

In one embodiment, an aperture to the organ is performed prior to stowing the applicator.

In another embodiment, an aperture to the organ is performed after fastening the applicator.

In one embodiment, the actuation is performed by a button.

In another embodiment, the actuation is performed by a serrated roller.

In one embodiment, the actuation is ordered by a radial toothed rack.

In another embodiment, the actuation is ordered by handle with a longitudinal toothed rack.

In one embodiment, the actuation is the sliding of an internal tube into an external tube.

In one embodiment, the fastening to the pneumoperitoneum is performed with a set of valves.

In another embodiment, the fastening to the pneumoperitoneum is performed with aspiration.

In one embodiment, the fastening to the pneumoperitoneum is performed with pliers with chuck jaws in either side of the elongated tube with sharp spikes.

In another embodiment, the fastening to the pneumoperitoneum is performed with teeth being curved radially and in an opposite direction at the extremities of internal and external tubes as to grasp the external wall of the digestive tract by simple rotation of these two tubes.

In an alternate embodiment, the fastening to the pneumoperitoneum is performed through a small tooth-needle fixed in the periphery of opposite sites two by two of the internal tubes. A thrust at a right angle slides during the actuation making contact of the internal tube with the external tube, teeth leave their housing, take the deployed form.

In another embodiment, the fastening to the pneumoperitoneum is performed by actuation of the internal tube relative to the external tube which opens and closes a circular network of small grips; the internal tube possesses a regular network of holes by which pass rivets; each rivet communicates between the tubes a the driveshaft articulating two arms interdependent of the external tube where the actuation of the internal tube actuates the network of claws.

In one embodiment, the internal tube and external tube are connected except for the hollow zone linked to an external aspiration device creating under aspiration a circumferential zone stowed to the organ.

In another embodiment, the internal tube and external tube are kept together by a network of rings which allows the aspiration under vacuum to fasten the laparoscopic instrument.

In one embodiment, the extremity of the external tube is divided into flexible arms with final pin with small release in the base.

In one embodiment, by sliding the internal tube inside the external tube deformed elastic arms are pushed radially outwards.

In another embodiment, elastic arms are fixed in the periphery of the external tube as stems of cylindrical section.

In another embodiment, rigid elbows with bent jaws are placed in the periphery of the external tube.

In one embodiment, the anatomical structure is imprisoned between the hooks after rotation of the external and internal tubes.

In one embodiment, the injection medical device is used through colonoscopy.

In another embodiment, the applicator is formed by an internal tube and an external tube with a flange shape base and both act as a syringe dislodging the device.

In one embodiment, an injection medical device is used as an endoscopy instrument.

In one embodiment, the injection device is enclosed in a flexible cartridge at the extremity of a guide tube.

In another embodiment, the injection device is enclosed in a hollow cylindrical cartridge with a convex flexible extremity.

In one embodiment, the device is fixed to the end of sheath in the extremity of the cartridge.

In another embodiment, a push rod actuates the cable of sheath.

In an additional embodiment, the cable slides the inside piston ejecting the device.

In one embodiment, the device is ejected with a piston.

In another embodiment, the piston is rigid.

In yet another embodiment, the piston is flexible.

BRIEF DESCRIPTION OF THE DRAWINGS

FIG. 13; illustrates general structure of a laparoscopic applicator for a modular magnetic anastomosis comprises:
(1) exterior tube
(2) interior tube
(3) scaling system
(4) actuation system
(5) stowing system FIG. 14; is the cross longitudinal perspective of the main body of the applicator.

FIG. 15; illustrates external view of actuation system.

FIG. 16; describes a cross longitudinal view of the actuation system with different components that operate the mechanical movement and rotation of serrated roller.

FIG. 17; illustrates different components that operate the mechanical movement and rotation of the serrated roller.

FIG. 18; illustrates an alternative form of serrated roller.

FIGS. 26, 27 and 28; describe a laparoscopic applicator which is applied against the surface to be deployed by aspiration.

FIG. 29; illustrates an applicator with exterior and interior tubes in contact with series of rings.

FIGS. 38, 39 and 40; represent laparoscopic applicator that external and interior tubes of the applicator are fitted together with teeth being curved radially and in opposite direction.

DETAILED DESCRIPTION OF THE INVENTION

Figure 1:
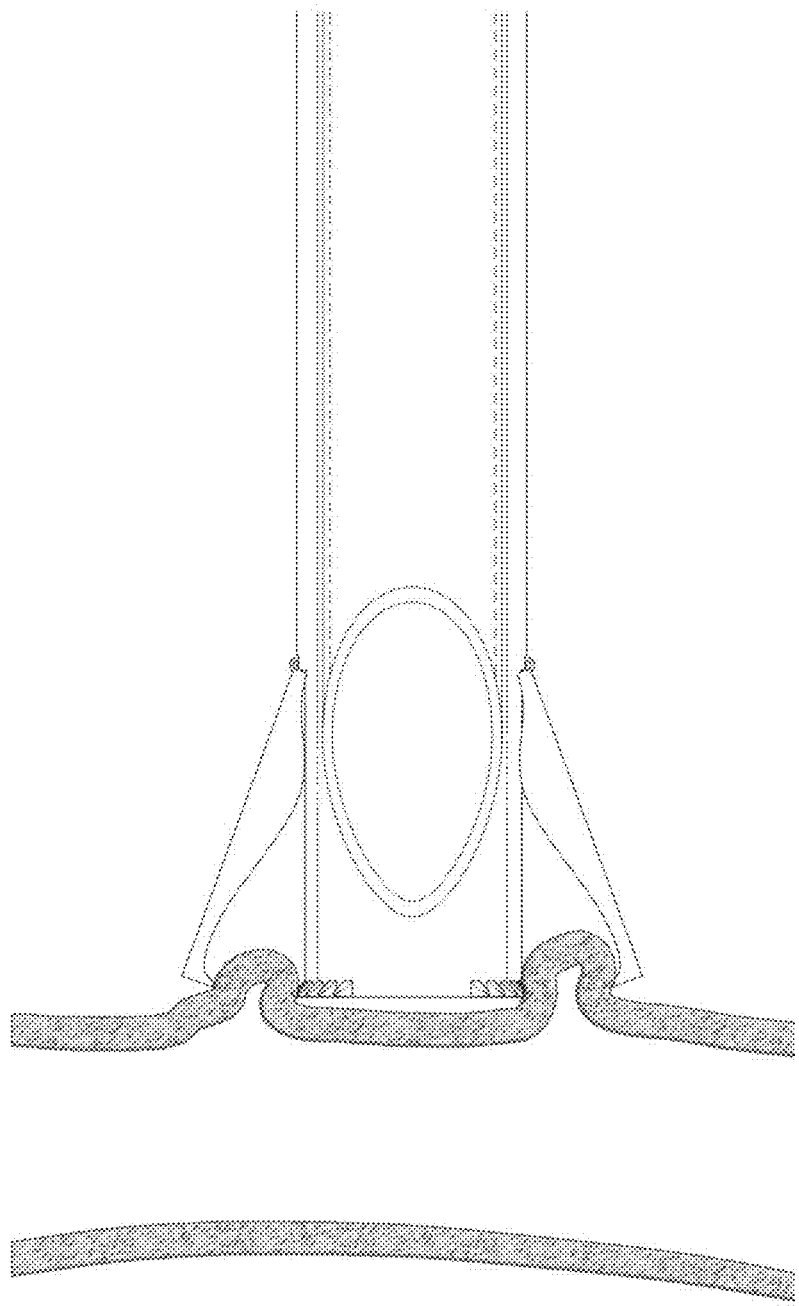
FIG. 1; illustrates an applicator for a modular magnetic anastomosis device using a laparoscopic technique with tightness valves for maintaining the pneumoperitoneum.
Figure 2:
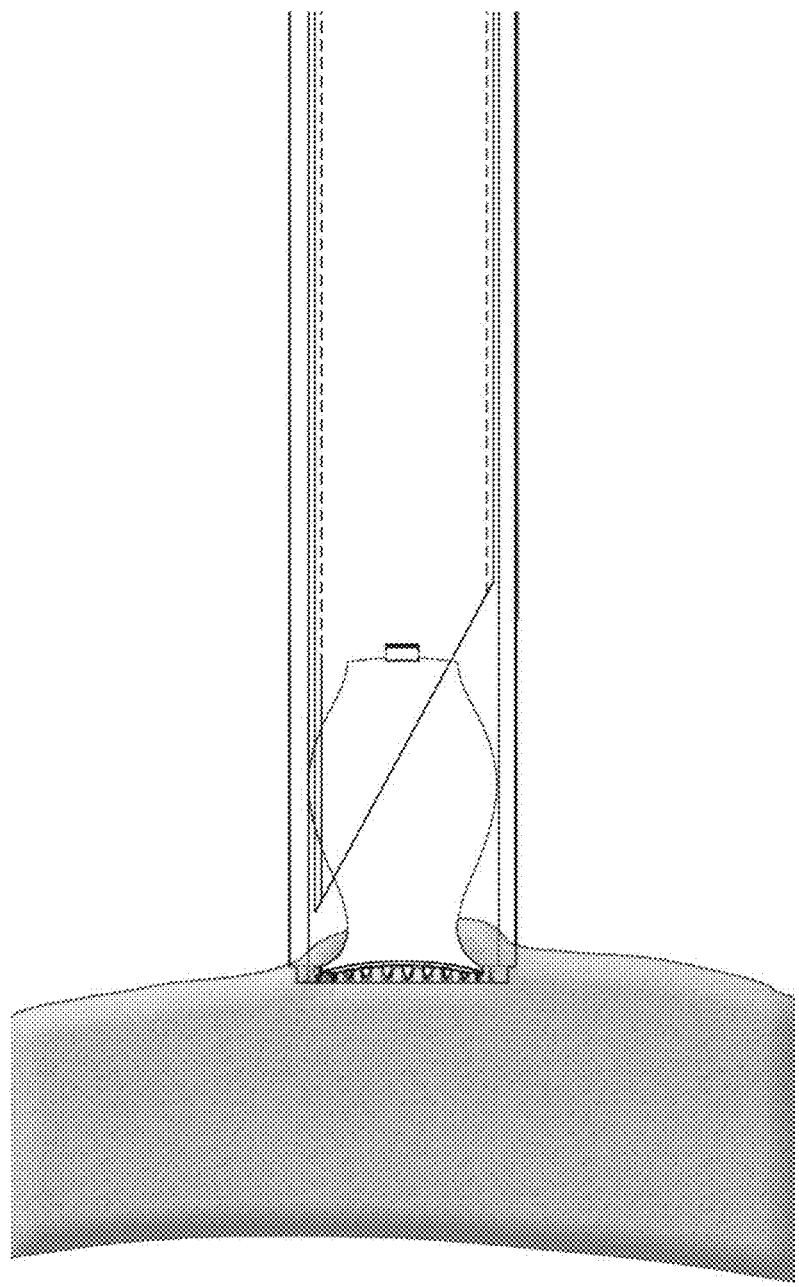
FIG. 2; is a side view of the laparoscopic applicator of the modular magnetic anastomosis device.
Figure 3:
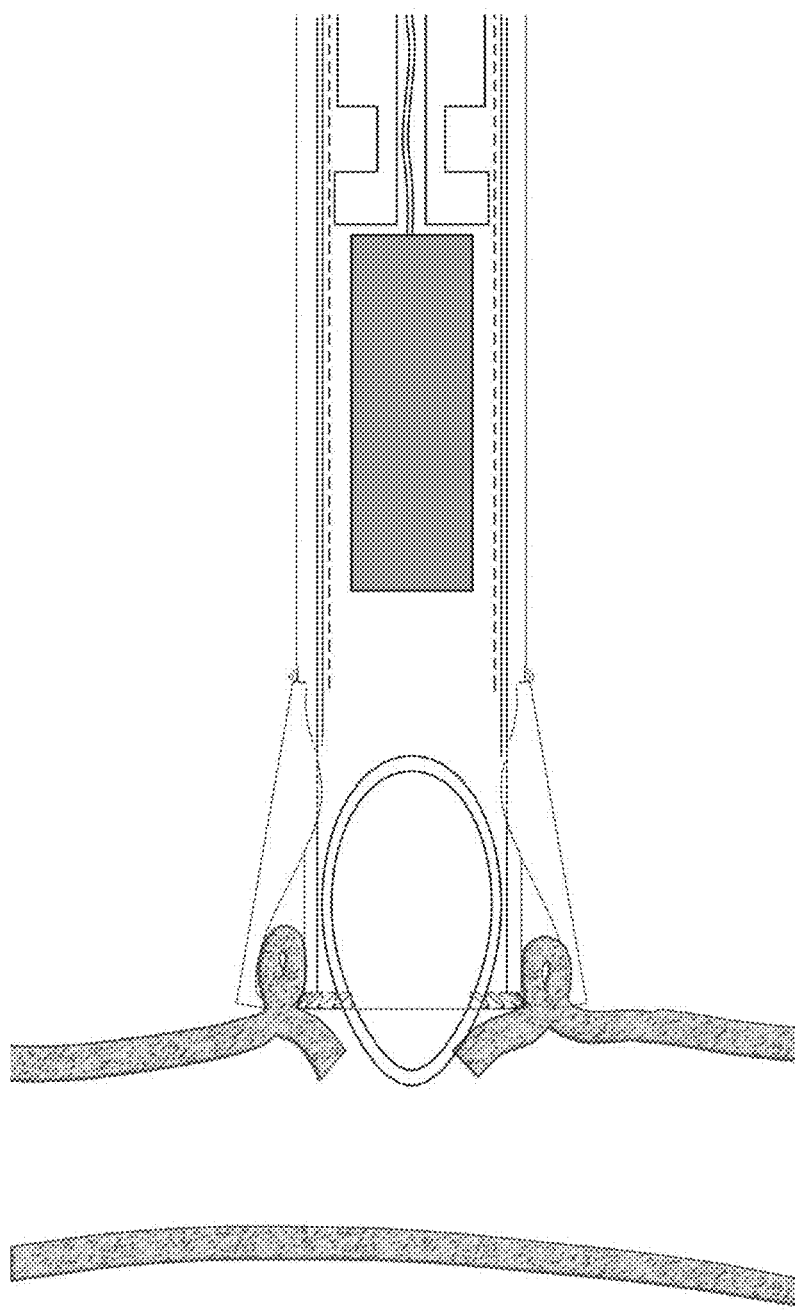
FIG. 3; describes a cross longitudinal perspective of the main body of the applicator, with the second beveled and sharpened tube and the arrangement of modular magnetic anastomosis device inside of the second glide tube.

Minimally invasive single site surgery (MISS) or natural orifice transluminal endoscopic surgery (NOTES™) are terminologies to explain the novel concept of scarless surgery which are increasingly making their way into clinical practice. Laparoscopic and endoscopic surgeries are well-established alternatives to open surgery for anastomosis. In general, the benefits of laparoscopy and endoscopy on postoperative pain, cosmetic benefits, hospital stay and convalescence are widely recognized. Central to the performance of MISS or NOTES surgery is the ability to achieve efficient and effective access to the surgical area of interest via a single port of entry using an endoscopic, percutaneous or laparoscopic applicator.

The MISS surgery approach has the potential to advance the field of percutaneous intra- and transluminal surgery. By direct percutaneous entry into hollow organs such as the urinary bladder, stomach and colon, newer intra- and transluminal procedures could be developed. The potential advantages of this approach would include operating within a localized pneumoviscerum environment (e.g., pneumovesicum, pneumogastrum or pneumocolum) in contrast to a generalized pneumoperitoneum, thereby potentially allowing certain major abdominal procedures to be performed under regional rather than general anesthesia.

The development priorities to meet future needs of MISS surgery are evenly divided across four categories: ports, instruments, optics and robotics. Of late, there has been a new entry to MISS surgery platforms: Single-Port Instrument Delivery Extended Research (SPIDER™ developed by TransEnterix Inc., Research Triangle Park, N.C., USA). It has been proposed that by instrument manipulation past the level of the skin and fascia, the local wound inflammation would be minimized compared with standard laparoscopy. Surgeons from IRCAD, Strasbourg, performed the first transvaginal NOTES™ cholecystectomy in humans in 2007. Since then, many NOTES™ procedures have been performed for varied indications using one or two instruments for dissection and retraction introduced through the transumbilical rigid trocars. They are primarily labeled as "Hybrid-NOTES." It is a win-win situation for both of these surgical access techniques (MISS and NOTES™) as they compensate for the disadvantages of each other and still adhere to the concept of "scarless" surgery.

The use of laparoscopic tools can not only help avoid trauma by decreasing removal and reinsertion but can also reduce the number of incision required to perform a procedure. They also reduce the additional time that is not directly spent in helping the patient in the operating room (OR) and thus reduce the patient risk and costs. Jamshidi et al. demonstrated the safety and efficacy of magnetic compression anastomosis (magnamosis) devices for sutureless, full-thickness intestinal anastomosis with serosal apposition and without leaks in a pig model. They further comment that gradient compression is superior to uniform compression. Mechanical integrity of magnetic anastomosis was similar to, if not better than staple or suture counterparts. Endoscopically placed tick internal magnets with external magnetic guidance is a feasible and novel approach to creating gastroenteral anastomosis without abdominal incisions or sutures.

The IRCAD institute has developed a modular magnetic anastomosis device; the installation of the device requires a limited access compared to its useful surface after deployment. It can be placed accurately and in a minimally invasive fashion in any segment of the digestive tract; it allows realizing bypasses between all hollow viscera; it is also available in all useful sizes by the simple addition of magnetic elements according to the anatomical structure on which it has to be implemented. In its non-deployed shape, the system can be placed inside a small sized channel. It can be placed on a guide-tread and inserted into an access device such as a catheter.

The present invention relates to an applicator and methods particularly useful for delivery of injection medical device in a minimally invasive single site surgery (MISS), natural orifice transluminal endoscopic surgery or colonoscopy surgery (NOTES™).

The laparoscopic instruments are functioning as a hopper. In contact with the surface to be deployed, the hopper preserves the pressure on the pneumoperitoneum; using standard instruments before or after stowing according to the alternatives aperture is created; and the device is introduced to the internal organ by a flexible or rigid piston according to the alternatives. The upper parts of these laparoscopic instruments are formed in a similar fashion and a set of valves ensures the sealing and the conservation of the pneumoperitoneum; except for the alternatives presented in FIGS. 26 to 29, where the fixation is assured using aspiration. The principal structure of the alternatives are two tubes: one internal tube enveloped by an external tube with radial or longitudinal relative movement; wherein the relative movement is ordered by a button, a serrated roller or a handle actuating a radial or longitudinal toothed rack; or simply by manual sliding motion of the two tubes as represented in FIGS. 30 to 35. The sliding motion of the external and interior tubes actuates various mechanism of fixation located at the end of the device.

Figure 4:
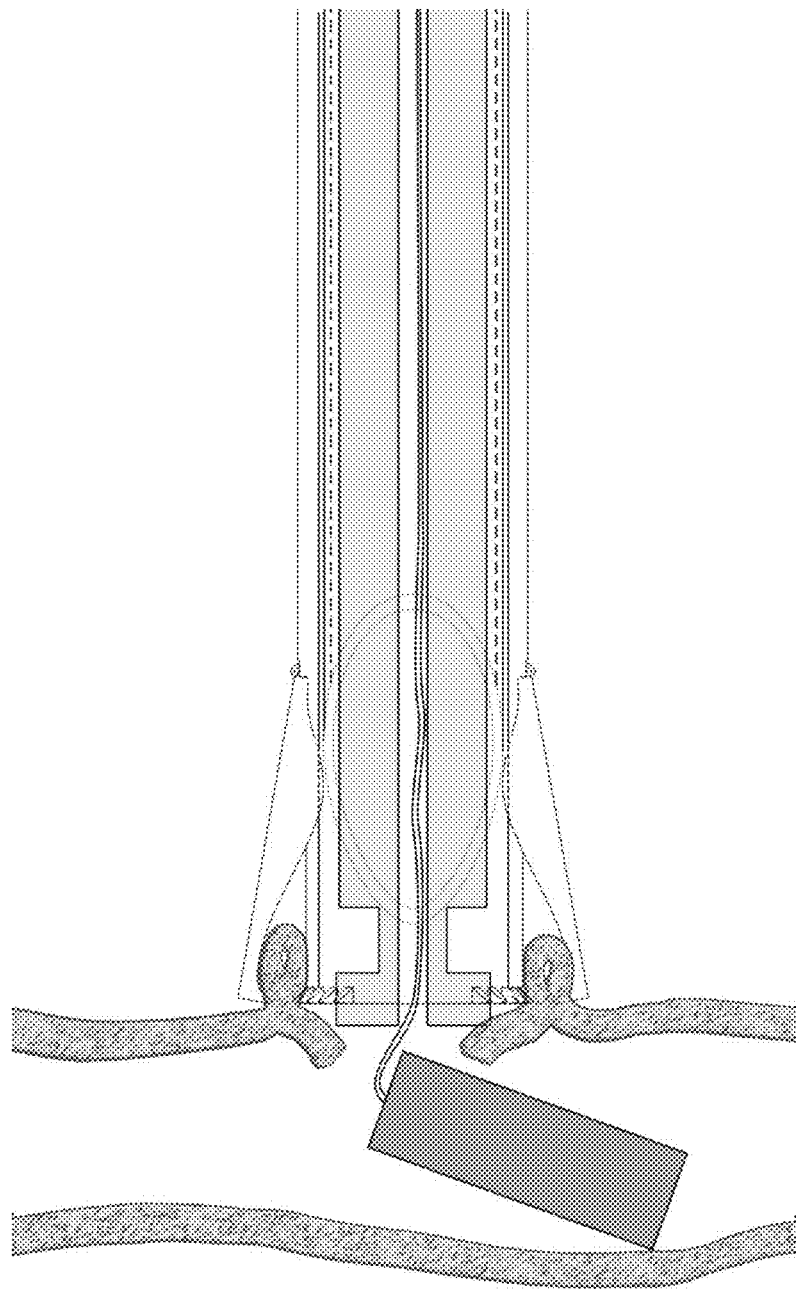
FIG. 4; illustrates the ejection of the anastomosis device with the wire guide from the laparoscopic applicator in the non-deployed configuration.

FIG. 1 to FIG. 4 present one variant of an applicator for the modular anastomosis device; where the delivery instrument is a laparoscopic applicator with an extremity possessing tightness valves maintaining the pneumoperitoneum for inserting or retrieving the various parts of the anastomosis device or tools for the procedure. The main body of the applicator 1.4 is an elongated tube; pliers with chuck jaws are placed on either side of the elongated tube, presented in FIGS. 1.2 and 2.2. The extremity of this elongated tube possesses sharp spikes acting as intermediary chuck jaws for the pliers 1.1 and 3.1. A second beveled and sharpened tube is presented in 1.3, 2.3 and 3.3; this second tube glides inside the first one and is used to cut the wall. The modular anastomosis device is logged into the second tube illustrated in 3.6 and is ejected to the organ to be deployed using a plunger presented in 3.5. FIG. 4 illustrates the modular magnetic anastomosis device with the wire guide ejected from the laparoscopic applicator.

Figure 5:
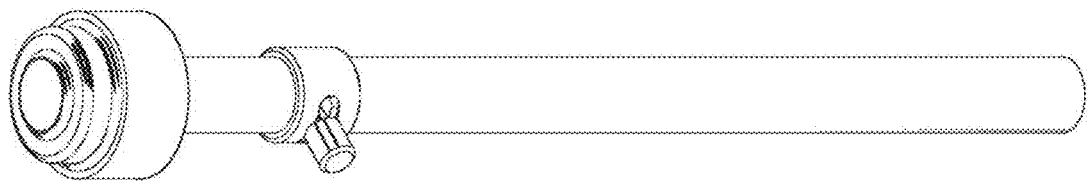
FIG. 5; describes a variant of the laparoscopic applicator where the main body of the applicator and the internal tube are fitted together with a tightness valve and an external button for opening and closing the applicator.
Figure 6:
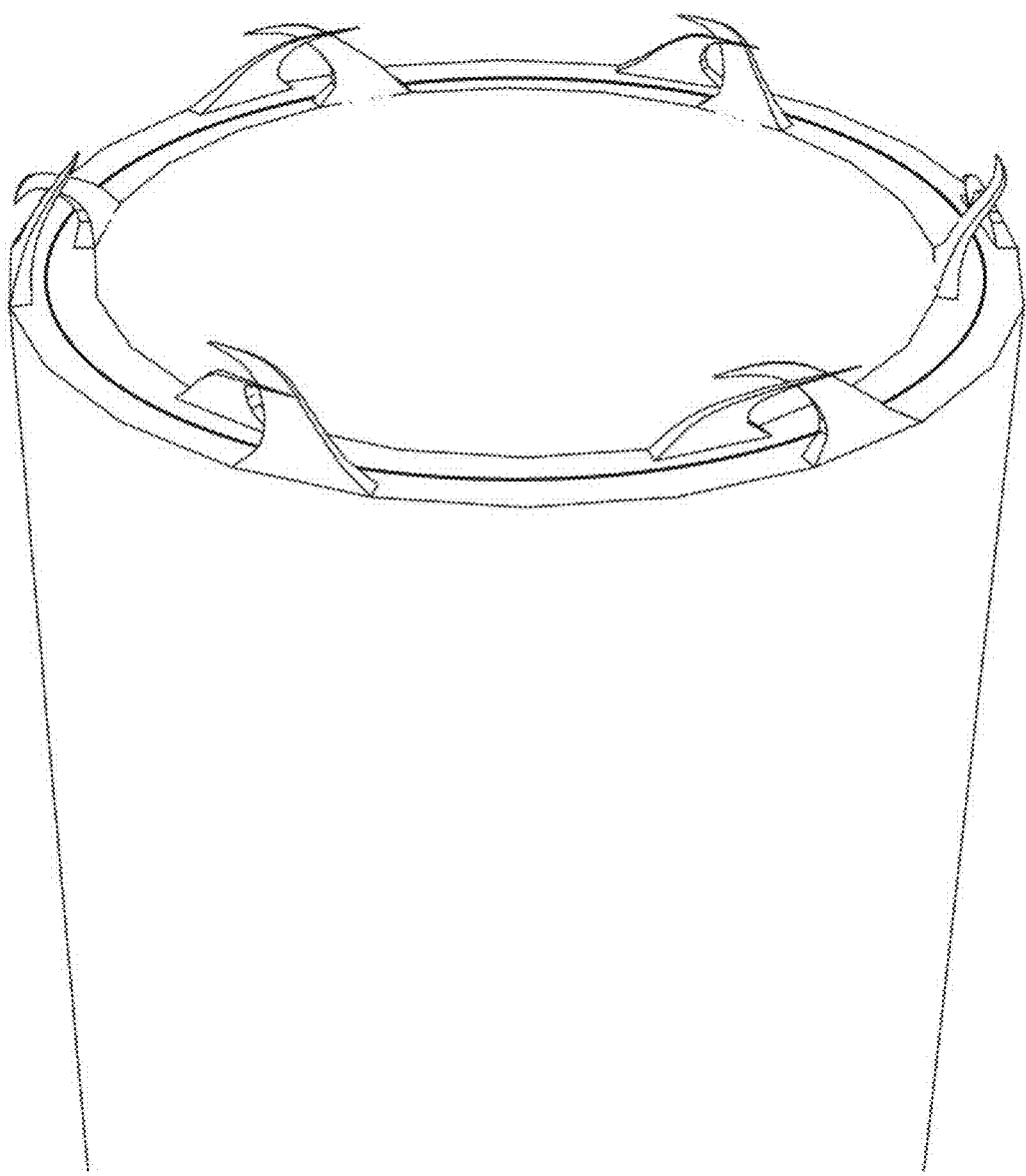
FIG. 6; shows a cross section of the main body of the applicator fitted with the internal secondary tube with teeth being curved radially and in opposite direction.
Figure 7:
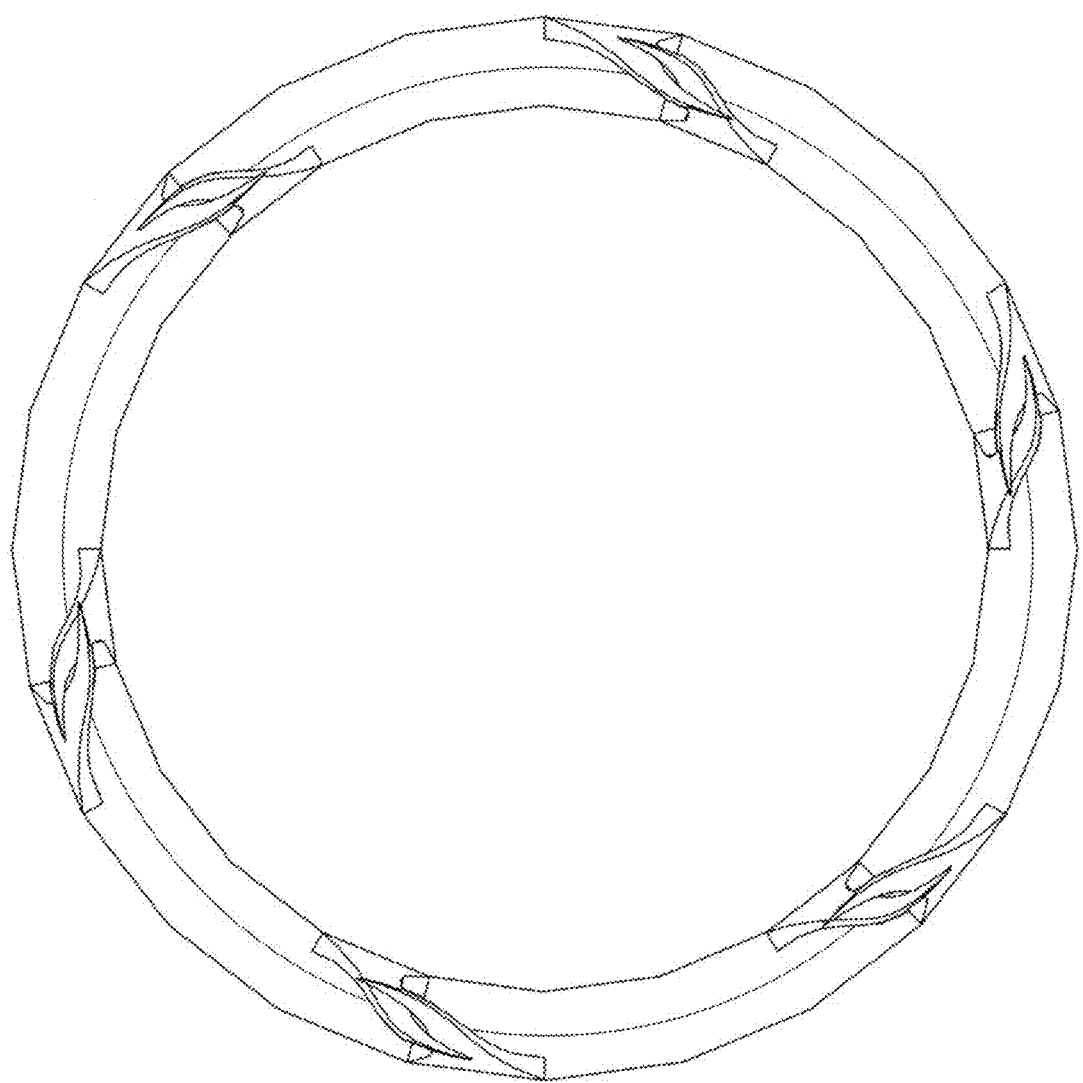
FIG. 7; is a presentation of the interaction between the teeth of the main body and the second internal tube of the applicator.
Figure 8A:
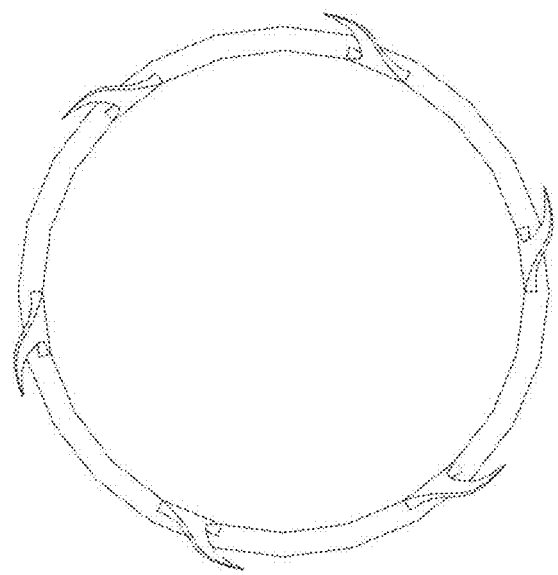
FIG. 8A-B; shows separately inner and outer tubes with general orientation of teeth.
Figure 8B:
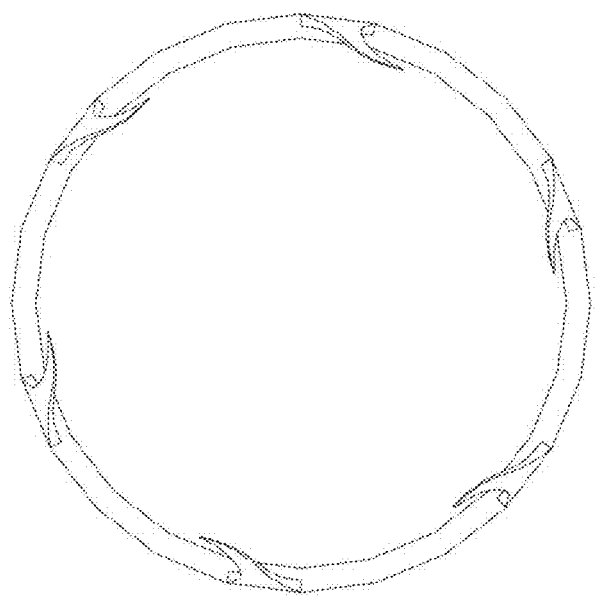

In a different variant, the laparoscopic applicator possesses a main body with a second internal tube fitted together. FIG. 5 illustrates this form of the device; 5.1 presents the basis with tightness valves allowing to maintain the pneumoperitoneum for insertion or retrieving the various parts of the modular anastomosis device or tools used to carry out the procedure. FIG. 6 shows the main body of the applicator 6.1, and the internal tube is shown in FIG. 6.2. Extremities of both of these tubes are teeth 6.3 being curved radially and in an opposite direction as to grasp the external wall of the digestive tract by simply rotating both tubes represented in FIG. 7. The teeth are maintained in a closed position with a blocking mechanism using springs or tension ribbons resisting to the opening of the applicator jaws shown in 8.1 and 8.2. The open and closed positions of the applicator are maneuvered by a button or a handle on the external part of the applicator, as illustrated in 5.2.

Figure 9:
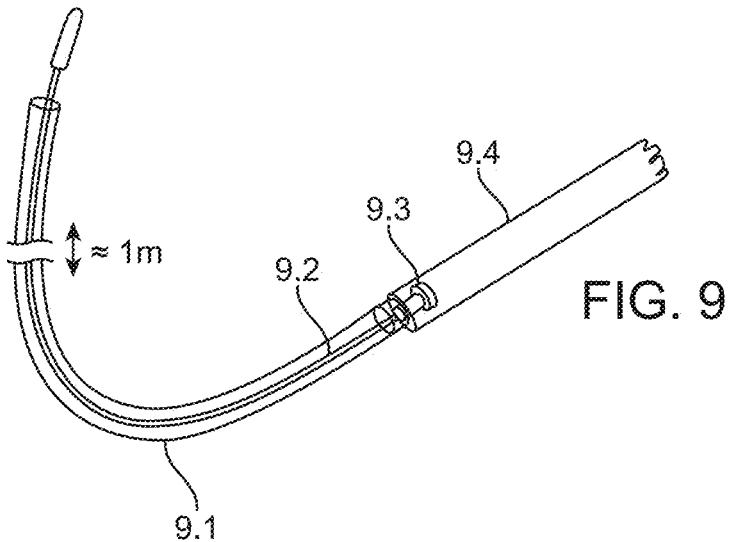
FIG. 9; shows the modular magnetic anastomosis device applicator used in endoscopy with the flexible cartridge enclosing the device.
Figure 10:
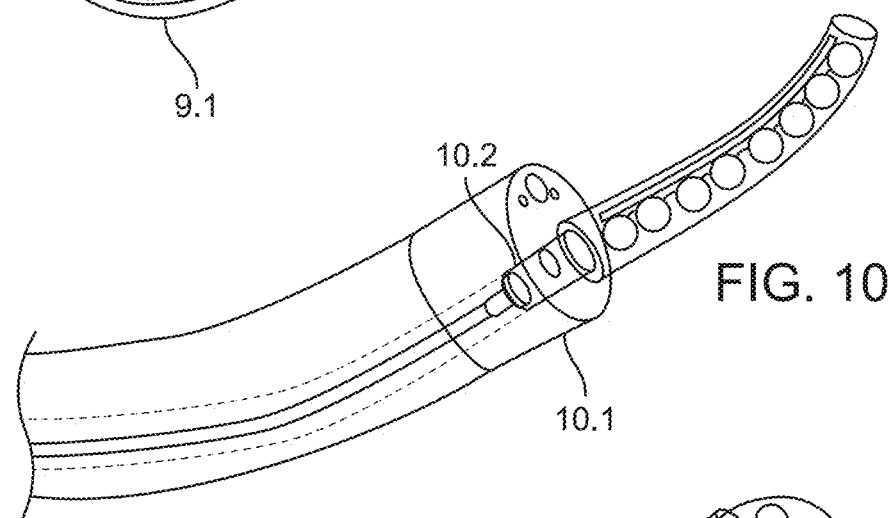
FIG. 10; illustrates the presence of the applicator used in an endoscope.
Figure 11:
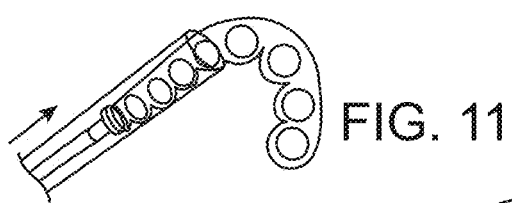
FIG. 11; shows the plunger pushing and thus ejecting the modular magnetic anastomosis device out of the flexible cartridge of the endoscopic applicator.
Figure 12:
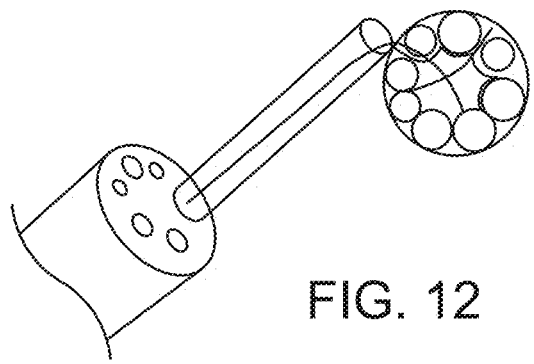
FIG. 12; presents the anastomosis device in its deployed configuration using the wire guide to close the device.

The non-deployed modular magnetic anastomosis device requires limited access compared to its useful surface after deployment, and it can be placed inside a small sized channel and be used by being inserted into an operating channel of the endoscope. FIG. 9 illustrates the various parts of such an applicator, composed of a guide tube 9.1 which is placed inside the operating channel of the endoscope to which is fitted a flexible cartridge 9.4 which encloses the modular magnetic anastomosis device. The device is deployed in the transplant organ by injecting it out from the flexible cartridge via a plunger 9.3 that is moved using a cable 9.2. FIG. 10 describes an endoscope 10.1 and the channel 10.2 with the cartridge ejected. FIGS. 11 and 12 illustrate the ejection of the anastomosis device from the cartridge and the final deployed circular modular magnetic anastomosis device.

A general structure of a laparoscopic applicator is described in FIG. 13 formed by an exterior tube (1), interior tube (2), sealing system (3), actuation system (4), stowing system (5); FIG. 14 is a cross longitudinal view of the applicator.

A structure of one of the actuation systems is described in FIGS. 15, 16 and 17. wherein the different components that operate the actuation system (4) make a translational movement between (1a) and (2a) by the rotation of serrated roller (9). In an alternative structure of the actuation system, presented in FIG. 18, the rotational movement between (1b) and (2b) by the rotation of the serrated roller (9) and a truncated end (8b) on the toothed circular section (10) is illustrated.

Figures 19, 20:
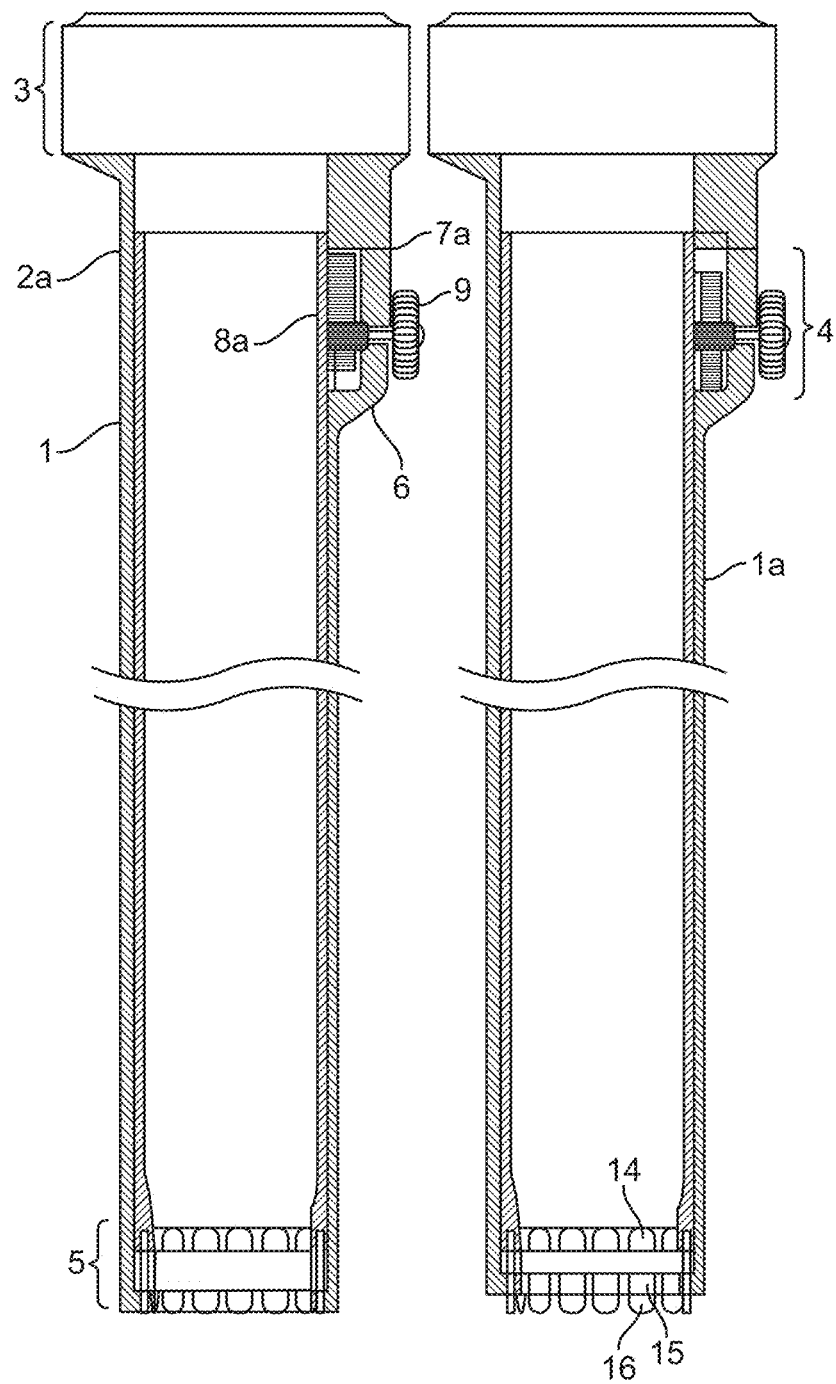
FIGS. 19 and 20; describe a laparoscopic applicator that the stowing system comprises a network of small tooth-needles.
Figures 21, 22:
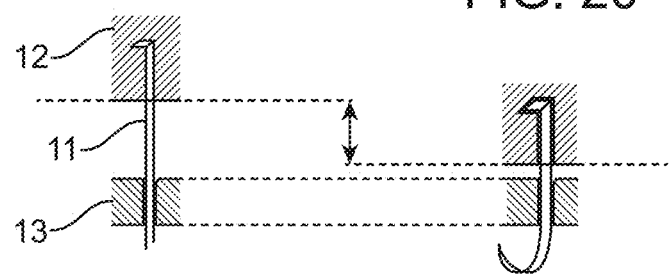
FIGS. 21 and 22; illustrate introduction of tooth-needle and deployed form of the tooth-needle after the laparoscopic applicator is fixed to desired anatomic surface.

One variant of a stowing system (5) is described in FIGS. 19 and 20, where the attachment system is through a network of small tooth-needles (11) fixed in the periphery of opposite sites two by two (14) of the internal tube (2a) a thrust at an right angle (12) slides during the actuation of the serrated roller (9) in small release (13) forming the end (15) of the external tube (1a). The contact of the extremities of the internal tube (14) with the external tube (15); teeth (11) leave their housing (13), take the deployed form presented in FIGS. 21 and 22 and for two by two the interior loops clutched to the organ to be fastened.

Figure 23:
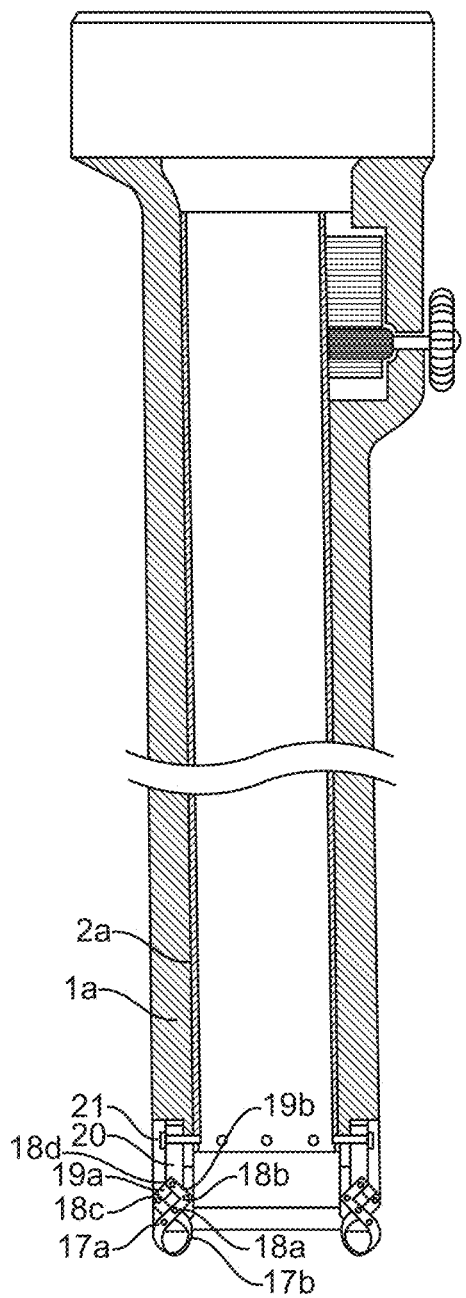
FIGS. 23, 24 and 25; present a laparoscopic applicator where the mechanical movement after stowing the application to desired organ opens and firm a circular network of small grips.
Figure 24:
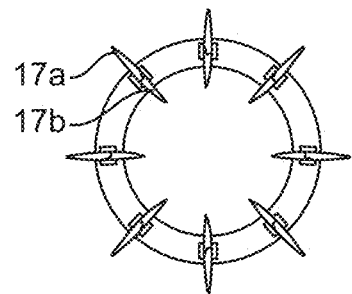
Figure 25:
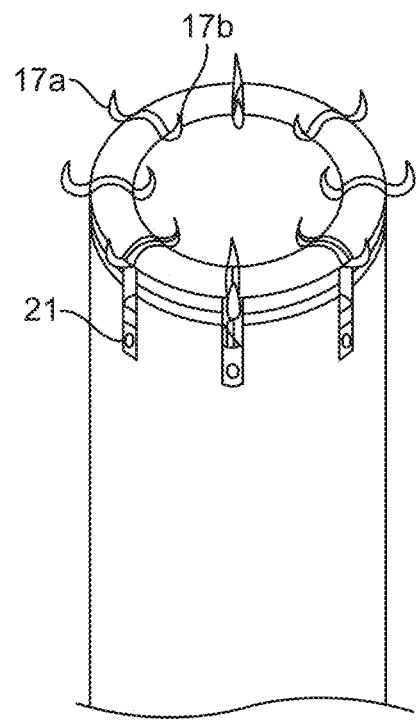
Figure 30:
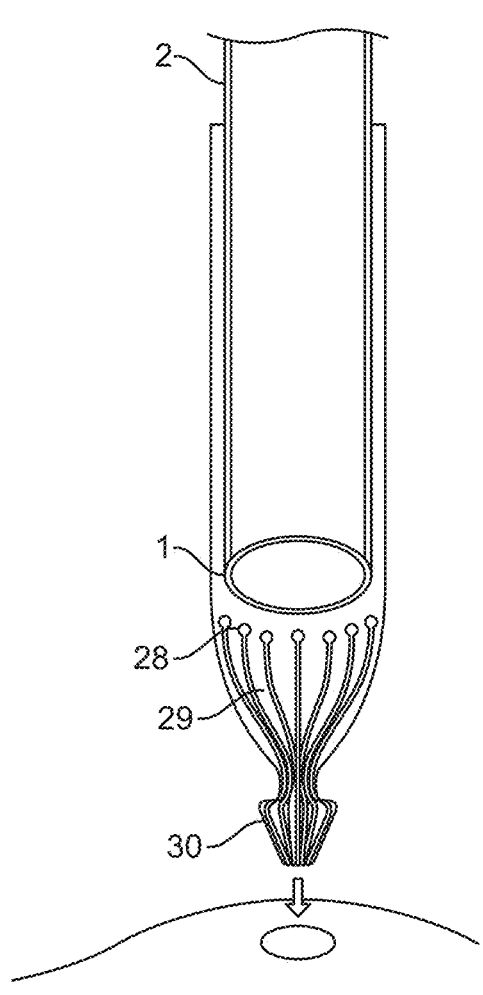
FIGS. 30 and 31; illustrate an applicator with an extremity divided in several resilient flexible or non ferromagnetic metal arms with final spur.
Figure 31:
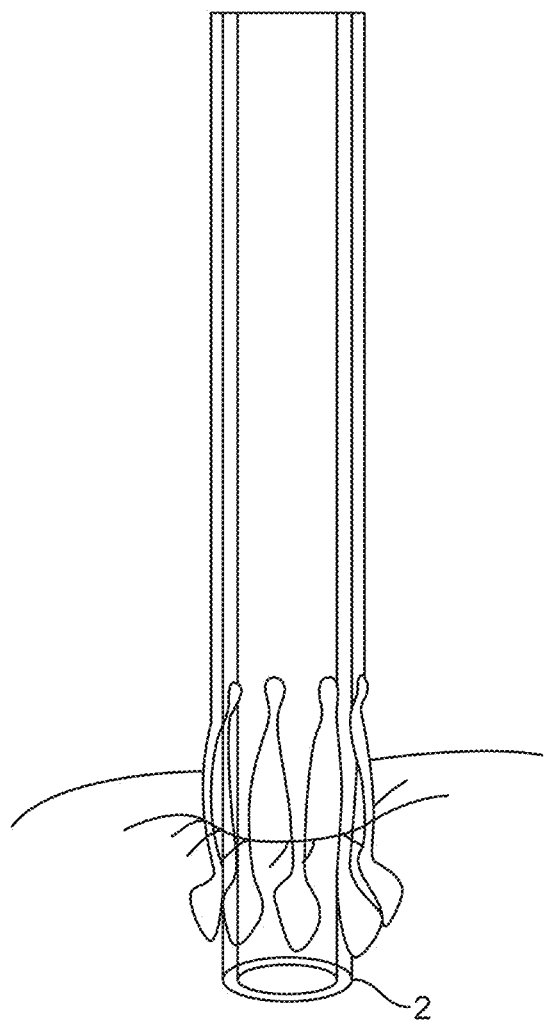
Figure 32:
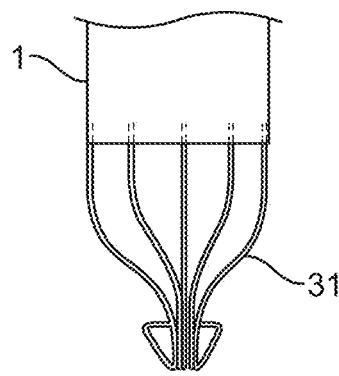
FIG. 32; illustrates the applicator that possessing stems of cylindrical sections allowing the fixation of the laparoscopic applicator after entry.

The change in stowing part (5) in another variant is presented in FIGS. 23, 24 and 25, wherein the actuation of the internal tube (2a) compared to the external tube (1a) opens and closes a circular network of small grips. The extremity of the internal tube (2a) possess a regular network of holes by which rivets pass (21); each rivet communicates between the internal tube (2a) and the driveshaft (20). The arm (20) articulates two intermediate arms (19 a) and (19b) on the axis (18d); these two grip (17a) and (17b) are constrained in the axis of rotation (18a), which is interdependent of the external tube (1a); in addition they are connected to the arms (19a) and (19b) by rivets (18b) and (18c); displacement of the internal tube (2a) jointly moves the grips (17 a) and (17b) and actuates the network of claws.

In a variant of a laparoscopic device the attachment to the organ is assured by a mechanism of aspiration under vacuum. FIGS. 26, 27, 28, and 29 illustrate such an applicator; the figures describe a unique tubular structure (1d) that replaces the internal and external tubes; a hollow zone (23) linked to a nozzle (22) linked to an external aspiration tube connected to an external device; the extremity of the device (24) under aspiration on a circumferential zone is fixed to the surface to be stowed. FIG. 29 shows the variant with external and internal tubes (1c) and (2c) that are maintained in position by a network of rings (25), which are bored with holes (26) allowing the aspiration under vacuum.

Figure 33:
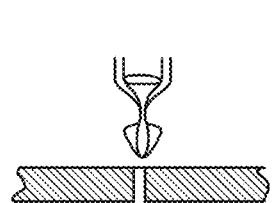
FIGS. 33, 34 and 35; illustrate the deployed form of laparoscopic applicator describe in FIGS. 30 and 31 and 32.
Figure 34:
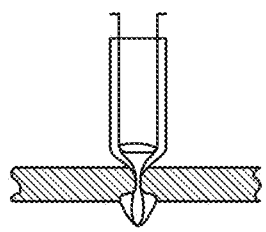
Figure 35:
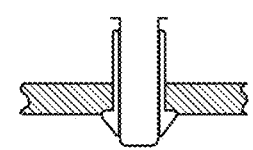

In another variant of a laparoscopic applicator the aperture for the surgery is carried out in the anatomical organ before fastening the applicator. FIGS. 30 to 35 describe such an applicator; the extremity (1) is divided into several flexible arms (29) with a final pin (30); the small release (28) in the base of (29) guarantees the flexibility of the spacing and the distal pin (30) is inserted in the opening. The actuation process is the sliding of tube (2) into the external tube (1); the arms (29) become deformed elastically and are pushed back radially by tube (2) in order to fasten this applicator to the anatomical structure. An alternative is presented in FIG. 32, where the elastic arms (31) are stems of cylindrical sections, fixed (1) by any means useful and performed to achieve the same function. FIGS. 33, 34 and 35 describe the operational mode.

Figures 36, 37:
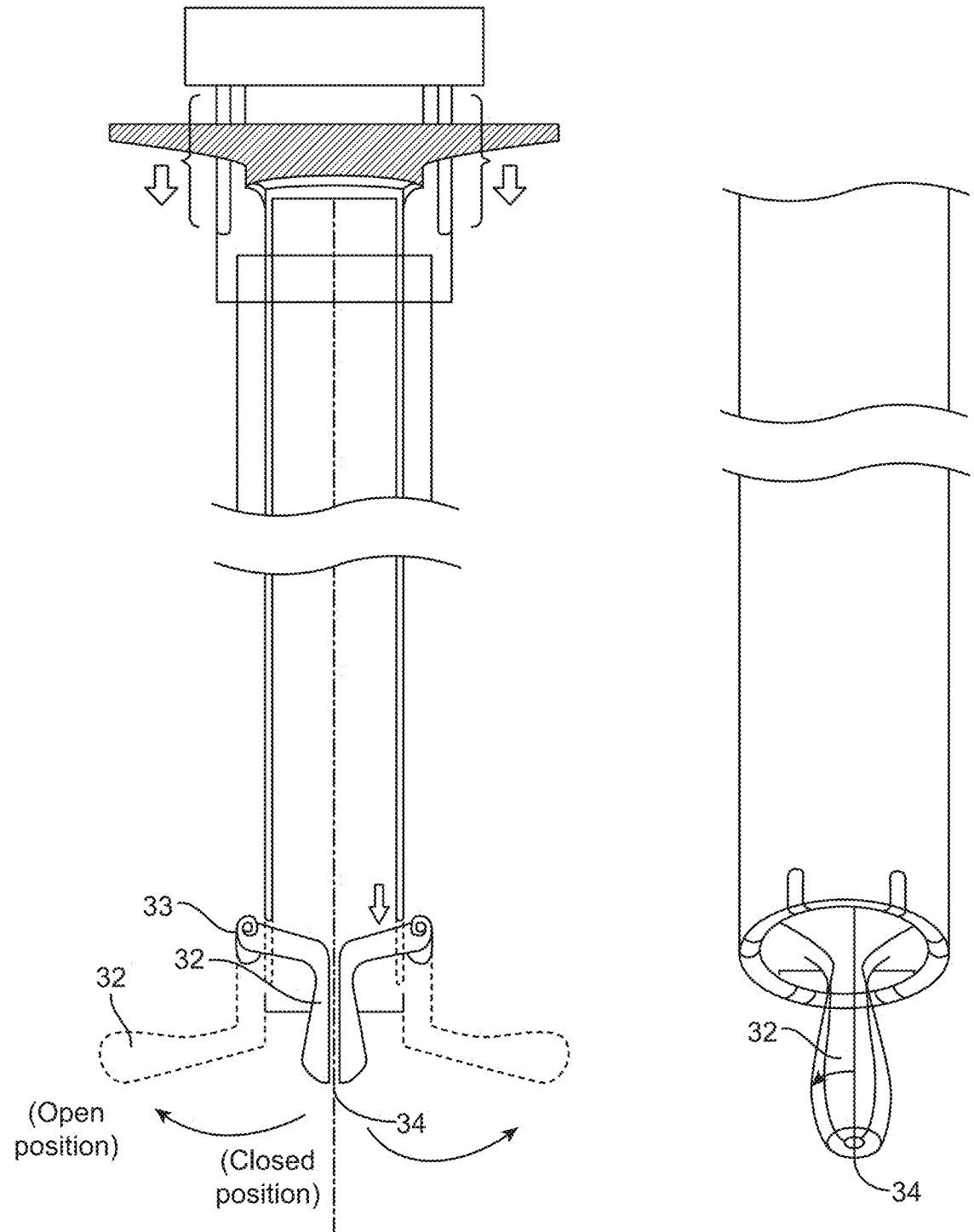
FIGS. 36 and 37; illustrate an applicator with rigid articulate hooks.

A variant of the previous applicator wherein the elastic strains are replaced with rigid elbows is described in FIGS. 36 and 37. In this alternative mode, several bent jaws (32) are fixed to the external tube (1). By a combination of rotation (33) and sliding of the internal tube (2), tube (1) pushes back (32) radially toward the outside and is fastening the instrument to the desired organ.

The geometry of the two tubes (32) induces a closed position and a central nozzle (34) allows the sliding of a wire-guide.

A variant of an laparoscopic applicator wherein said applicator is attached to the surface before opening an aperture, is depicted in FIGS. 38, 39 and 40; the external tube (1b) and internal tube (2b) with a rotational move as illustrated in FIG. 38; extremities of the tubes (1b) and (2b) possess a circular network with an equal number of small hooks, respectively (35) and (36) bent one towards the other in such a way that actuation in rotation (2b) relative to (1b) seizes and imprisons the anatomical structure to which the applicator is fastened.

Figure 41:
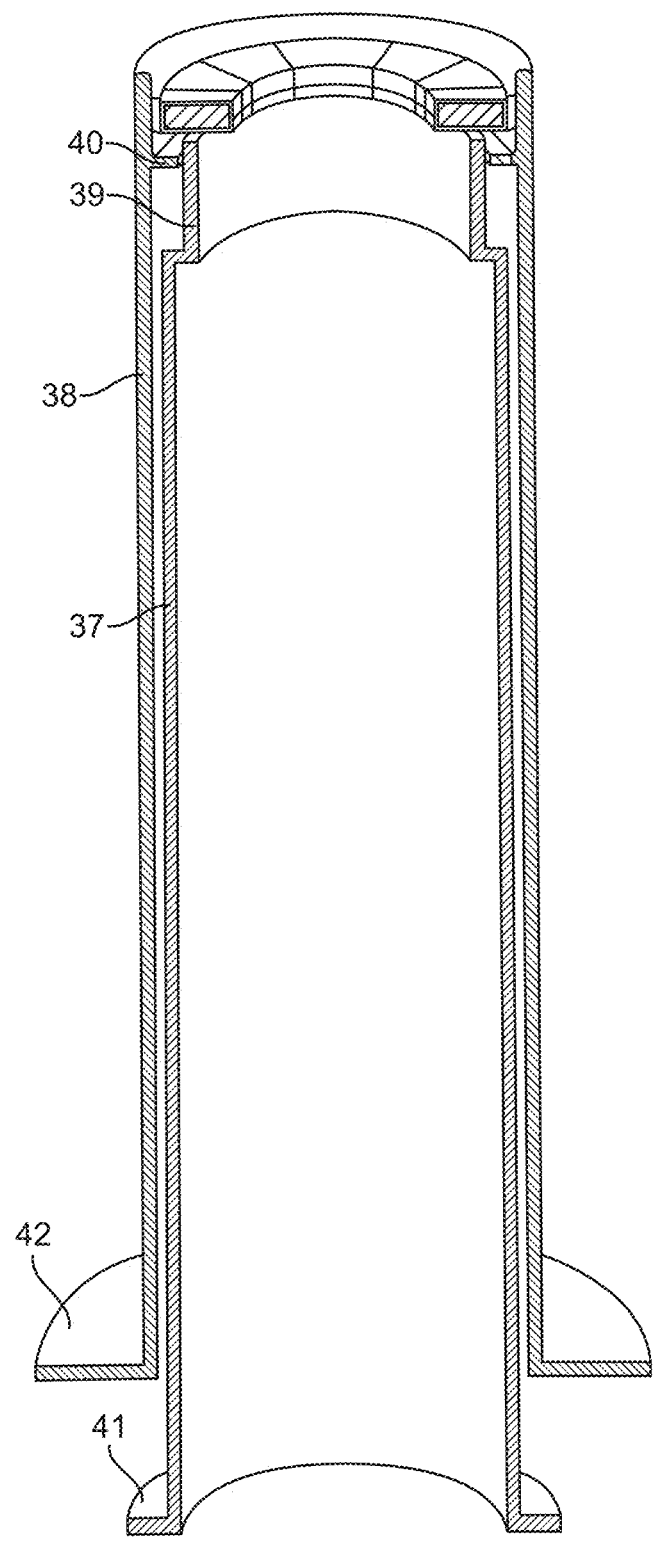
FIG. 41; describes a colonoscopy applicator for modular magnetic anastomosis.

FIG. 41 presents an alternative applicator for use as a magnetic anastomosis device such as described in WO2013/009886 A1 using a natural orifice, such as the colon. This applicator is formed by an internal tube (37) and an external tube (38); their bases in the shape of a flange (41) and (42) to allow the sliding of (37) in (38) such as in a syringe and dislodging the anastomosis device; a boring (40) in the interior of (38) retains the anastomosis device in a functional position; the push of (41) towards (42) resulting in the ejection of the anastomosis device and tightening (39) at the end of the internal tube.

Figure 42:
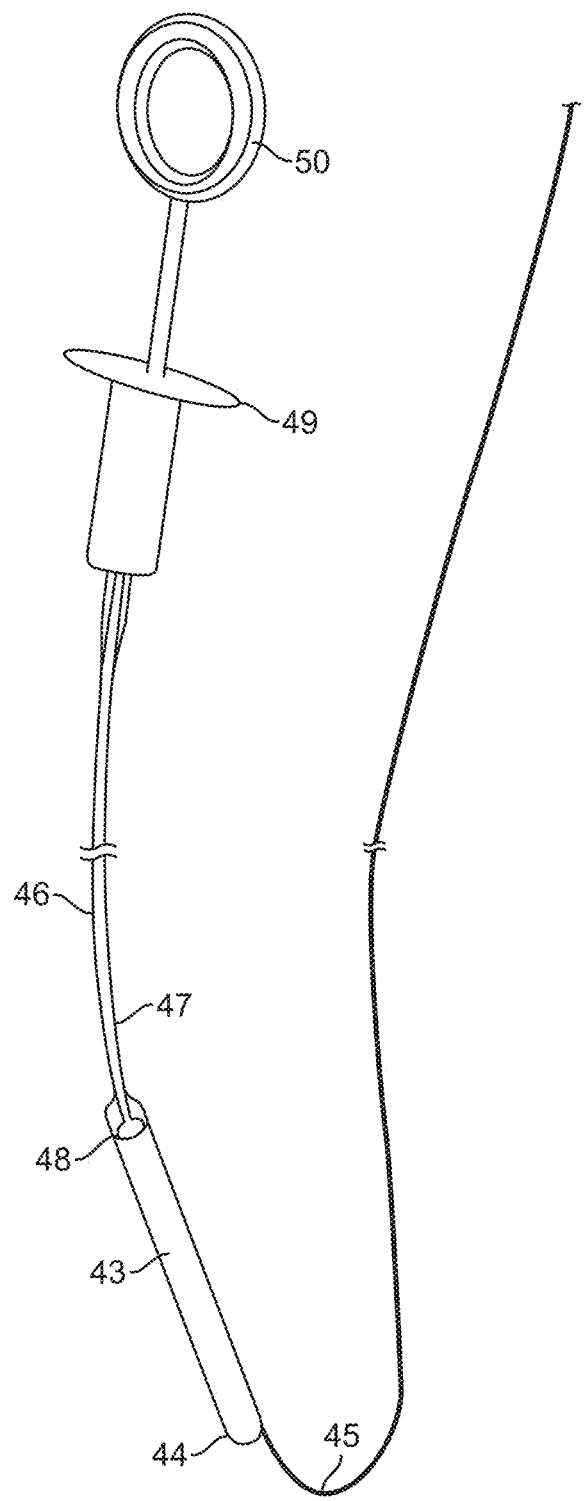
FIG. 42; shows a variant of modular magnetic anastomosis device applicator used in endoscopy with the flexible cartridge enclosing the device.

FIG. 42 presents an endoscopic variant of the applicator, which consists of a hollow cylindrical cartridge (43) with a convex extremity enclosing the device to be released; a flexible and extensible opening (44) is at the extremity of the cartridge (43) which is fixed to the ending (49) of a sheath (46), in this sheath circulates a cable (47) by actuating a push rod (40); the cable (47) slides the piston (48) inside of (43) ejecting the device contained in (43).

What is claimed is:

1. A surgical system comprising:
    (a) a modular magnetic anastomosis device configured to be introduced to an internal organ, wherein the modular magnetic anastomosis device is configured to form a circular anastomosis device and comprises two or more magnets enclosed in a flexible cartridge, and wherein the modular magnetic anastomosis device is ejectable; and
    (b) an applicator for delivery of the modular magnetic anastomosis device to the internal organ during minimally invasive surgery, wherein the applicator comprises:
        (1) a first elongated tube comprising a first hollow lumen connecting a first proximal end and a first distal end, wherein the first distal end comprises one or more teeth housings;
        (2) a second elongated tube comprising a second hollow lumen connecting a second proximal end and a second distal end, wherein the second elongated tube is enveloped by the first elongated tube, and wherein the second distal end comprises one or more tooth-needles;
        (3) a sealing system, wherein the sealing system comprises a valve which is configured to prevent air from escaping through the applicator when the applicator is placed into a peritoneal cavity and the peritoneal cavity is insufflated with air; and
        (4) an actuation system connecting the first proximal end and the second proximal end, wherein the actuation system is configured to cause the ejection release of the modular magnetic anastomosis device when the modular magnetic anastomosis device is at least partially within the applicator and the actuation system is actuated,
    wherein the one or more tooth-needles are configured to leave the one or more teeth housings to clutch and fasten the distal end of the first elongated tube to the internal organ.

2. The surgical system of claim 1, wherein the second hollow lumen is configured to receive the modular magnetic anastomosis device.

3. The surgical system of claim 1, wherein the actuation system is configured to cause a translational movement between the first elongated tube and the second elongated tube.

4. The surgical system of claim 1, wherein the actuation system is ordered by a member selected from the group consisting of a button, a serrated roller, a handle actuating a radial toothed rack, and a handle actuating a longitudinal toothed rack.

5. The surgical system of claim 1, wherein the second elongated tube is configured so that a sliding of the second elongated tube in the direction of the distal end causes the tooth-needle to leave the teeth housing.

6. The surgical system of claim 1, wherein the one or more tooth-needles are configured to form a hook-or loop-shape after leaving the teeth housing.

7. The surgical system of claim 6, wherein the one or more tooth-needles are configured to form a radially curved-shape.

8. The surgical system of claim 1, wherein the applicator of the ejectable modular magnetic anastomosis device further comprises a laparoscopic instrument.

9. The surgical system of claim 1, wherein the modular magnetic anastomosis device is configured to be delivered by the applicator through a natural orifice.

10. The surgical system of claim 1, wherein the modular magnetic anastomosis device comprises an endoscopic instrument.

11. The surgical system of claim 1, further comprising a piston formed from a rigid or flexible material.

12. The surgical system of claim 1, wherein the one or more tooth-needles are retractable and extendable.

* * * * *

UNITED STATES PATENT AND TRADEMARK OFFICE
CERTIFICATE OF CORRECTION

| | | |
|---|---|---|
| PATENT NO. | : 12,161,339 B2 | Page 1 of 1 |
| APPLICATION NO. | : 16/861050 | |
| DATED | : December 10, 2024 | |
| INVENTOR(S) | : Juan Hernandez and Michele Diana | |

It is certified that error appears in the above-identified patent and that said Letters Patent is hereby corrected as shown below:

In the Claims

In Claim 6, Column 8, Line 47, please insert a space between 'hook-' and 'or'.

Signed and Sealed this
Tenth Day of June, 2025

Coke Morgan Stewart
*Acting Director of the United States Patent and Trademark Office*